United States Patent
Hwang et al.

(10) Patent No.: US 7,041,125 B2
(45) Date of Patent: May 9, 2006

(54) COIL REINFORCED CATHETER INNER TUBULAR MEMBER

(75) Inventors: Jason J. Hwang, Seattle, WA (US); Marc L. Speck, Temecula, CA (US); Hanh V. Hoang, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 377 days.

(21) Appl. No.: 10/186,769

(22) Filed: Jul. 1, 2002

(65) Prior Publication Data

US 2004/0002727 A1 Jan. 1, 2004

(51) Int. Cl.
*A61F 2/06* (2006.01)

(52) U.S. Cl. .................................... 623/1.11
(58) Field of Classification Search ............... 606/194, 606/108; 623/1.11; 604/523–527
See application file for complete search history.

(56) References Cited

U.S. PATENT DOCUMENTS

| | | | | |
|---|---|---|---|---|
| 4,981,478 A | * | 1/1991 | Evard et al. ................. | 604/527 |
| 5,728,065 A | * | 3/1998 | Follmer et al. ........... | 604/96.01 |
| 5,951,539 A | * | 9/1999 | Nita et al. ................... | 604/526 |
| 6,165,163 A | * | 12/2000 | Chien et al. ................. | 604/523 |
| 6,193,686 B1 | * | 2/2001 | Estrada et al. .......... | 604/103.09 |
| 6,511,462 B1 | * | 1/2003 | Itou et al. ................... | 604/264 |
| 6,669,886 B1 | | 12/2003 | Willard | |

* cited by examiner

*Primary Examiner*—(Jackie) Tan-Uyen T. Ho
(74) *Attorney, Agent, or Firm*—Fulwider Patton LLP

(57) ABSTRACT

A catheter having an elongated shaft formed of a polymeric tube with at least a section having an outer coiled support member wound in a first direction and embedded in the polymeric tube, and an inner coiled support member wound in a second direction opposite to the first direction. In a presently preferred embodiment, the inner coiled support member has coils spaced closer together than coils of the outer coiled support member. In one embodiment, the inner coiled support member is partially embedded in the polymeric tube.

24 Claims, 2 Drawing Sheets

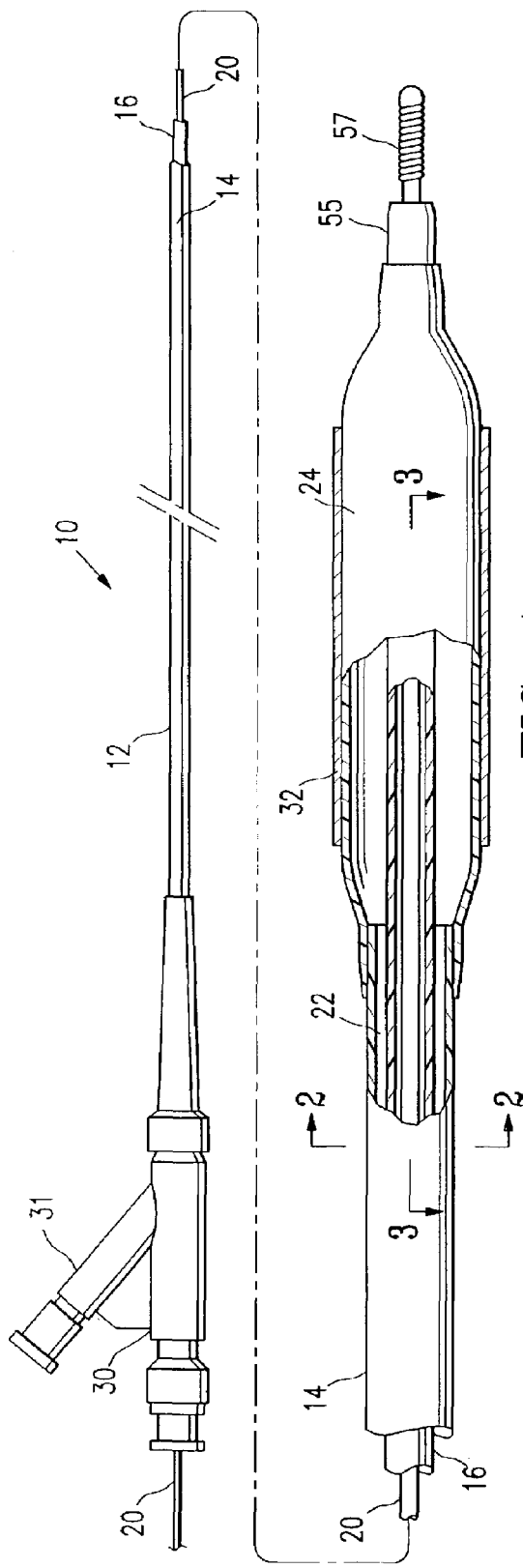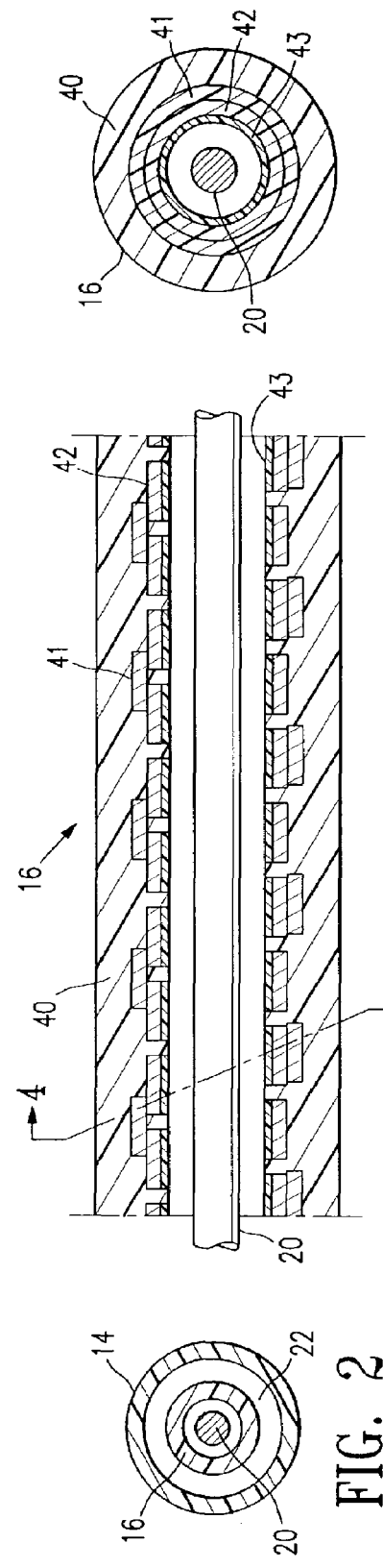

COIL REINFORCED CATHETER INNER TUBULAR MEMBER

BACKGROUND OF THE INVENTION

This invention generally relates to catheters, and particularly intravascular catheters for use in percutaneous transluminal coronary angioplasty (PTCA) or for the delivery of stents. In percutaneous transiuminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau, et al.) and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter) and flexibility to be readily advanceable within the tortuous anatomy of the patient's vasculature. Conventional balloon catheters for intravascular procedures, such as angioplasty and stent delivery, frequently have relatively a stiff proximal shaft section to facilitate advancement of the catheter within the patient's body lumen and a relatively flexible distal shaft section to facilitate passage through tortuous anatomy such as distal coronary and neurological arteries without damage to the luminal wall.

To help meet the desire for a catheter having sufficient pushability, while maintaining trackability, prior art designs have supplemented polymer catheter shafts with a stiffening wire or mandrel. Other prior art designs have addressed these handling and performance issues by suggesting use of materials of different stiffness or reinforcements in the proximal and distal portions of the catheter shaft. Despite these attempts, prior art designs have suffered from various drawbacks. For example, support mandrels do not always transmit axial force effectively.

Accordingly, it would be a significant advance to provide a catheter having improved pushability while maintaining good flexibility. This invention satisfies these and other needs.

SUMMARY OF THE INVENTION

The invention is directed to a catheter having an elongated shaft formed of a polymeric tube with at least a section having an outer coiled support member wound in a first direction and embedded in the polymeric tube, and an inner coiled support member wound in a second direction opposite to the first direction. In a presently preferred embodiment, the inner coiled support member has coils spaced closer together than coils of the outer coiled support member. In one embodiment, the inner coiled support member is partially embedded in the polymeric tube.

In a presently preferred embodiment, the catheter is a balloon catheter. The balloon catheter of the invention may comprise a variety of suitable balloon catheters, including coronary and peripheral dilatation catheters, stent delivery catheters, drug delivery catheters, and the like. A balloon catheter of the invention generally comprises an elongated shaft with an inflation lumen, a guidewire receiving lumen, a proximal shaft section defining a proximal portion of the inflation lumen, and a distal shaft section defining a distal portion of the inflation lumen, with an inflatable balloon on the distal shaft section having an interior in fluid communication with the inflation lumen. At least part of the guidewire receiving lumen extends within the distal shaft section to a guidewire distal port in the distal end thereof. In one embodiment, the catheter is a rapid exchange type catheter having a guidewire distal port at the distal end of the catheter, a guidewire proximal port in the distal shaft section spaced a relatively short distance proximally from the guidewire distal port and a relatively long distance from the proximal end of the catheter shaft, and a relatively short guidewire receiving lumen extending between the proximal and distal guidewire ports in the distal shaft section. In an alternative embodiment, the catheter is an over-the-wire type catheter having an elongated shaft with proximal and distal ends, a guidewire port in the proximal end, a guidewire port in the distal end, and a guidewire lumen extending therein from the distal end to the proximal end of the catheter shaft.

In a presently preferred embodiment, the balloon catheter elongated shaft comprises an outer tubular member defining an inflation lumen, and an inner tubular member within the outer tubular member lumen and defining a guidewire lumen, and the inner tubular member is formed of the polymeric tube having the outer and inner coiled support members in accordance with the invention. The inner coiled support member is tightly wound with coils which are either closed together (i.e., stacked) or with a small space therebetween. The closely wound coils of the inner coiled support member provide excellent pushability. The outer coiled support member is more loosely wound with coils which are spaced apart. The angle or pitch of the coils of the outer coiled support member is therefore greater than the pitch of the inner coiled support member coils, and preferably is at least about 25 degrees greater than the pitch of the inner coiled support member coils. The absolute pitch and the difference in pitch between the inner and outer coiled support members are selected to provide an improved combination of high tensile spring rate and high flexibility. The upper limit of the pitch of the outer coil is driven by the allowable bending stiffness of the inner member. Higher absolute (and higher delta) pitches will continue to increase the tensile stiffness and strength but the penalty is an increasing bending stiffness. The tensile spring rate (k) is understood in the art to refer to the ratio of force generated per unit length of extension, typically measured by stretching the spring with a force gage attached thereto to measure the force resulting from stretching the spring a given distance. The high tensile spring rate provides improved axial stiffness and strength facilitating retraction of the catheter from the patient's vasculature. The difference in pitch increases the tensile spring rate. However, the absolute pitch of the outer coiled support member increases the bending stiffness of the catheter shaft. As a result, the pitch of the inner coiled support member is preferably minimized, so that the absolute pitch of the outer coiled support member can be selected to be sufficiently low to provide excellent flexibility, while the difference in pitch is still great enough to provide a high tensile spring rate. The pitch of the outer coiled support member is typically not greater than about 40 to about 60 degrees with respect to the longitudinal axis of the tube to provide sufficient flexibility, and the difference in pitch between the inner and outer coiled support member coils is about 25 to about 45 degrees to provide a preferred tensile strength and stiffness. In one embodiment, the pitch of the outer coiled support member expressed, in mils, is about 50 to about 100 mils, and the difference in pitch between the inner and outer coiled support members is about 25 to about 60 mils (for a shaft inner diameter of about 0.017 inches and a wire width of about 0.002 inches). However, the pitch in mils will vary depending on the size of the shaft and the width of the coiled wire or ribbon.

In a presently preferred embodiment, the coiled support members are a flat member such as a ribbon, although a variety of cross sectional shapes may be used including wire members having round or oval cross sections. The coiled support members are preferably formed of a high modulus material such as metal, carbon fiber, and polymeric materials such as Kevlar and liquid crystal polymers including Vectran. In a presently preferred embodiment, at least one of the coiled support members is formed of a metal such as a stainless steel, or super elastic alloy including a nickel-titanium (Nitinol) alloy.

In a presently preferred embodiment, the shaft of the invention has an inner surface which is lubricious. The lubricious surface may be provided using a variety of suitable methods, including embedding the inner coiled support member in a lubricious polymer which forms at least an inner layer of the shaft, coating an inner surface of the shaft with a lubricious polymer, or in the embodiment in which the inner coiled support member is only partially embedded in a nonlubricious polymer, coating the wire or ribbon of the inner coiled support member with a lubricious polymer. In one embodiment, a partially embedded inner coiled support member has a lubricious coating on at least an inner surface thereof. The lubricious coating facilitates guidewire movement in a guidewire lumen defined by the shaft. The coating provides a lower profile than is typically produced with a lubricious tubular liner on an inner surface of the inner tubular member. Thus, a lubricious liner would be also suitable, provided the liner has a sufficiently small wall thickness so that the overall diameter of the shaft is not disadvantageously increased by the liner. The lubricious coating can be applied before winding of the inner coiled support member, or thereafter as a dispersion coating of the inner tubular member lumen. In one embodiment, the lubricious coating is only on an inner surface of the inner coiled support member.

The catheter of the invention is highly pushable, flexible, trackable and kink resistant due to the coiled support members. The pitch and the difference in pitch of the outer and inner coiled support members provides an improved combination of flexibility (for trackability), and strength (compression and tension, for retractability and pushability). Moreover, the lubricious coating on the inner coiled support member provides an improved low profile shaft with excellent guidewire movement in the inner tubular member lumen. Additionally, the coiled support members preferably provide improved hoop strength to the inner tubular member, providing increases kink resistance and collapse resistance during delivery and inflation. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter which embodies features of the invention.

FIG. 2 is a transverse cross sectional view of the catheter shown in FIG. 1, taken along line 2—2.

FIG. 3 is an enlarged, longitudinal cross sectional view of the catheter shown in FIG. 1, taken along line 3—3.

FIG. 4 is a transverse cross sectional view of the catheter shown in FIG. 3, taken along line 4—4.

DETAILED DESCRIPTION OF THE INVENTION

Figure 5:
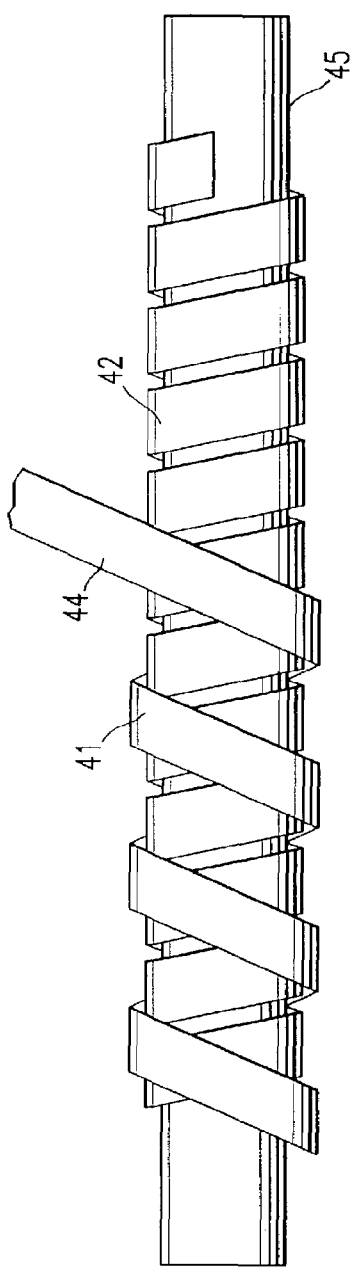
FIG. 5 is an elevational view illustrating the formation of the inner tubular member of the catheter shown in FIG. 1.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20. The coaxial relationship between outer tubular member 14 and inner tubular member 16 defines annular inflation lumen 22, as best illustrated in FIG. 2 showing a transverse cross section view of the distal end of the catheter shown in FIG. 1, taken along line 2—2. An inflatable balloon 24 disposed on a distal section of catheter shaft 12 has a proximal skirt section sealingly secured to the distal end of outer tubular member 14 and a distal skirt section sealingly secured to the distal end of inner tubular member 16, so that its interior is in fluid communication with inflation lumen 22. An adapter at the proximal end of catheter shaft 12 is configured to provide access to guidewire lumen 18, and to direct inflation fluid through arm 31 into inflation lumen 22. In FIG. 1, balloon 24 is illustrated in an unexpanded configuration prior to inflation thereof. In the embodiment illustrated in FIG. 1, an expandable stent 32 is mounted on uninflated balloon 24. The distal end of catheter may be advanced to a desired region of a patient's body lumen in a conventional manner and balloon 24 inflated to expand stent 32, and the balloon 24 deflated and the catheter withdrawn, leaving the stent 32 implanted in the body lumen.

As best illustrated in FIG. 3, showing an enlarged, longitudinal cross 10 sectional view of the catheter shown in FIG. 1, taken along line 3—3, inner tubular member 16 comprises a polymeric tubular member 40, an outer coiled support member 41 wound in a first direction and completely embedded in the polymeric tubular member 40, and an inner coiled support member 42 wound in a second direction opposite to the first direction. In the embodiment illustrated in FIG. 3, the inner coiled support member 42 is partially embedded in the polymeric tubular member 40. The terminology "partially embedded" should be understood to mean that at least part of the inner coiled support member is not covered by the polymeric tubular member 40. In the embodiment illustrated in FIG. 3, an inner surface of the inner coiled support member 42 directed toward the lumen 18 of the inner tubular member 16 is not covered by the polymer of the polymeric tubular member 40. FIG. 4 illustrates a transverse cross sectional view of the catheter shown in FIG. 3, taken along line 4—4.

A lubricious coating 43 is on an inner surface of the inner coiled support member 42. Preferably, the inner coiled support member has an outer surface in contact with an inner surface of the outer coiled support member. The coiled support members 41,42, wound in opposite directions, provide increased tensile properties and stiffness. Specifically, the outer coiled support member exerts a radially inward force on the inner coiled support member and interlocks therewith when the catheter is under tension (e.g., during retraction of the catheter), which increases axial stiffness and tensile strength.

In the embodiment of FIG. 3, the coiled support members 41, 42 are formed of a flat metal ribbon with a rectangular transverse cross section. However, a variety of suitable configurations may be used including a round or oval wire. The ribbon forming the support members has a width of about 0.001 to about 0.005 inches (0.025 to about 0.127 mm), preferably about 0.002 inches (0.051 mm), and a thickness of about 0.0005 to about 0.001 inches (to about 0.013 to about 0.025 mm), preferably about 0.0007 inches (0.018 mm). The coiled support members are preferably formed of a stainless steel or NiTi alloy (NITINOL). In a presently preferred embodiment, the stainless steel is a stainless steel having the highest available tensile strength. In one embodiment, the stainless steel is tempered. The ribbon or wire coiled support members may be unifilar (i.e., formed of a single filament), or multifilar (i.e., formed of multiple filaments connected together). The inner coiled support member is preferably unifilar, for improved low pitch. In one embodiment, the outer coiled support member is preferably multifilar to provide increased stiffness or strength. A multifilar outer coiled support member 41 having two filars would provide twice the tensile spring rate, and will increase the catheter bending stiffness (by about a factor of two) compared to a unifilar outer coiled support member 41. In one embodiment, an assembly in which inner coiled support member 42 and outer coiled support member 41 are both unifilar provides a tubular member having a spring rate of about 0.05 to about 1.5 lbs/inch. In another embodiment, an assembly in which the inner coiled support member 42 is unifilar and the outer coiled support member 41 is multifilar provides a tubular member having a spring rate of about 0.05 to about 10 lbs/inch.

In one embodiment, a ribbon or wire is wound in a first direction to form the inner coiled support member 42, and then a second ribbon or wire is wound in the opposite direction over the inner coiled support member to form the outer coiled support member 41. However, in an alternative embodiment a ribbon or wire is wound in a first direction to form the inner coiled support member 42 and then back over itself in the opposite direction to form the outer coiled support member 41, so that the inner and outer coiled support members 41, 42 are an integral, one piece unit. FIG. 3 illustrates one embodiment having two layers of coils formed by the inner and outer coiled support members. In alternative embodiments (not shown), the coil supported shaft may have one or more additional layers of coils, resulting in three or more coiled support members. In one embodiment, such additional coiled support members are wound in the same direction as the outer (second) coiled support member, with the same or different pitch as the outer coiled support member.

In the embodiment of FIG. 3, the coils of the inner coiled support member 42 have a pitch and spacing there between which is constant along the length of the inner coiled support member, as do the coils of the outer coiled support member 41. The inner coiled support member 42 has coils spaced closer together than the coils of the outer coiled support member 41. The coils of the inner coiled support member 42 are sufficiently close together to provide high axial push. The coils of the outer coiled support member 41 have a pitch which is about 10 to about 60 degrees, and preferably about 25 to about 40 degrees, and the coils of the inner coiled support member 42 have a pitch which is about 2 to about 15 degrees, and preferably about 2 to about 5 degrees. In a presently referred embodiment, the coils of the outer coiled support 41 member have a pitch which is about 10 to about 45 degrees, preferably about 25 to about 45 degrees greater than the pitch of the inner coiled support member 42. A unifilar ribbon having a thickness of 0.0007 inches and a width of 0.002 inches, wound to form the inner and outer coiled support members 41, 42, would produce a tubular member having a spring rate of effectively zero when the inner and outer coiled support members 41,42 have the same pitch, resulting in coils which unwind when the assembly is pulled (low tension strength). However, the same assembly would provide tubular member having sufficiently high spring rate of about 0.02 to about 1.0 lbs/inch when the pitch of the outer coiled layer is increased to about 10 to about 45 degrees greater than the pitch of the inner coiled layer, providing a catheter shaft with excellent tension and torsion properties. An assembly having an outer coiled layer with a pitch of about 32 degrees and an inner coiled layer with a pitch of about 2 degrees (delta pitch of about 30 degrees, having a spring rate of about 0.5 lbs/inch would provide a higher spring rate and a lower bending stiffness than an assembly having an outer coiled layer with a pitch of about 37 degrees and an inner coiled layer with a pitch of about 22 degrees (delta pitch of about 15 degrees, having a spring rate of about 0.22 lbs/inch, due to the smaller delta pitch, despite the high absolute pitch of the outer coiled layer.

In the embodiment of FIG. 1, the lubricious coating 43 has been applied to the ribbon forming the inner coiled support member 42, before the ribbon is wound, so that after the ribbon is wound the lubricious coating is only on the inner surface of the wound ribbon. Therefore, the lubricious coating 43 does not extend between adjacent spaced apart coils of the inner coiled support member 42, and as a result, the lubricious coating forms a discontinuous lubricious layer. Alternatively, the lubricious coating can be applied within the lumen 18 of the inner tubular member 16 after the ribbon is wound to form the coiled support members, in which case the lubricious coating would form a continuous lubricious layer. The lubricious coating 43 comprises a lubricious polymer commonly used in catheter design such as high density polyethylene (HDPE), parylene, or fluoropolymers including polytetrafluoroethylene (TEFLON). The lubricious polymer can be applied to the inner coiled support member 42 by a variety of suitable methods including dip coating, spray coating, and vacuum deposition. The lubricious coating 43 has a thickness of about 0.0025 to about 0.025 mm, preferably about 0.005 to about 0.0075 mm.

The polymeric tubular member 40 forms a matrix which holds the coiled support members and seals them to prevent air and contrast media from leaking through the coils. The polymeric material forming polymeric tubular member 40 may be selected to provide a desired property such as lubricity, or compatibility with adjacent catheter components to facilitate fusion bonding thereto. In a presently preferred embodiment, the polymeric tubular member 40 is formed of a polymer such as nylon. However, a variety of polymeric materials can be used including polyether block amide (PEBAX), HDPE, urethanes, and functionalized polyolefins such as Primacor. In one embodiment, polymeric tubular member 40 is formed at least in part of a lubricious polymer such as HDPE which, together with lubricious coating 43, enhances guidewire movement within the inner tubular member in the embodiment in which the inner coiled support member 42 has spaced apart coils. The polymeric tubular member 40 is typically an extruded tube positioned over the coiled support members which are wound on a mandrel, and heated to cause the polymeric tubular member to flow onto and around the outer coiled support member 41 and the outer surface of the inner coiled support member 42, to thereby form the inner tubular member 16. FIG. 5 illustrates formation of the inner tubular member by winding a ribbon 44 onto a mandrel 45 to form the coiled support members 41, 42, before the polymeric tubular member 40 is placed therearound. During assembly of the catheter 10, the end portions of the inner tubular member 16 are typically cut off or otherwise trimmed to provide the desired length of the inner tubular member 16. Therefore, during formation of the inner tubular member 16, the coiled support members typically have a shorter length than the polymeric tubular member 40, to thereby facilitate cutting the ends of the polymeric tubular member 40 to shorten the inner tubular member 16. After trimming, the length of the coiled support members may be the same as or shorter than the length of the polymeric tubular member 40.

Figure 6:
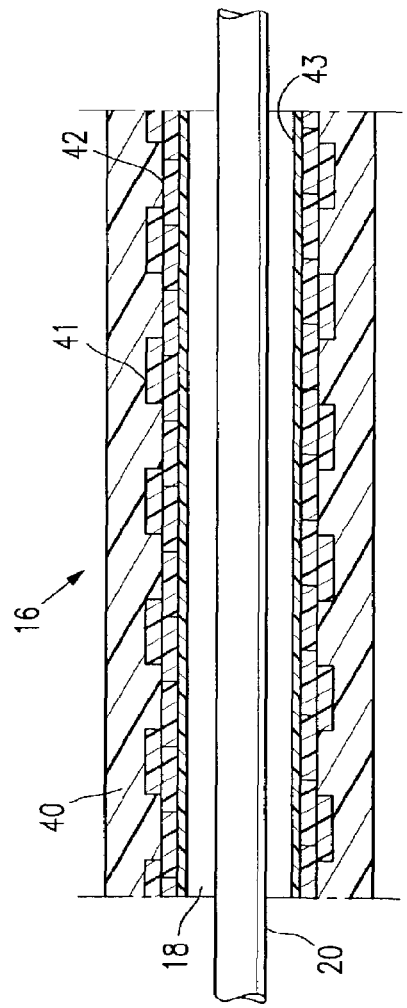
FIG. 6 is an enlarged, longitudinal cross sectional view of an alternative embodiment, having an inner coiled support member with stacked coils.
Figure 7:
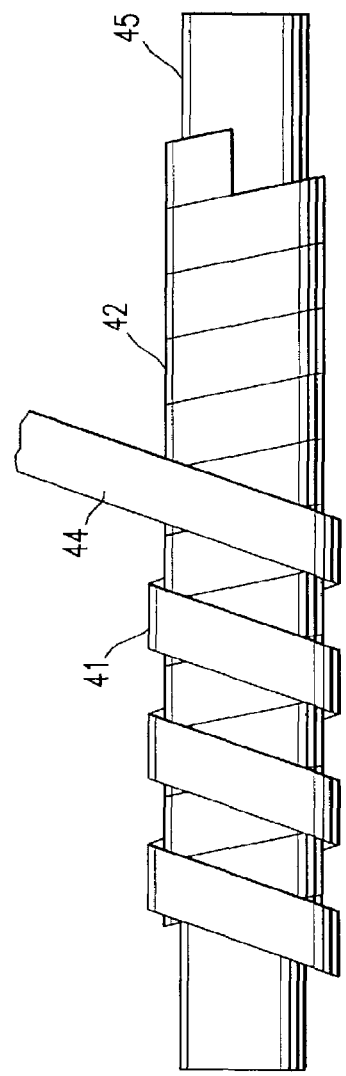
FIG. 7 is an elevational view illustrating the formation of the tubular member shown in FIG. 6.

In the embodiment of FIG. 3, the coils of the inner coiled support member 42 are spaced apart. FIG. 6 illustrates an alternative embodiment in which the coils of the inner coiled support member 42 are closed together in contact with one another, for improved transmission of force providing enhanced catheter pushability. FIG. 7 illustrates formation of the inner tubular member 16 of FIG. 6, in which ribbon 44 is wound onto mandrel 45 with stacked coils forming the inner coiled support member 42, and spaced apart coils forming the outer coiled support member 41.

When the catheter of the invention is used in an angioplasty procedure, the balloon catheter of the invention is advanced over the guidewire until the balloon is properly positioned across the stenosis within the patient's body lumen. The balloon can be inflated in a conventional manner by introducing inflation fluid through the inflation lumen. After one or more inflations, the balloon is deflated and the catheter removed from the patient. A similar procedure is used when the balloon has a stent mounted thereon for implanting the stent in the body lumen. The catheter of the invention is useful in a variety of applications including dilatation and stent delivery, and is particularly useful in coronary and neurovascular applications and other applications requiring a low profile, high inflation pressure catheter with excellent maneuverability.

To the extent not previously discussed herein, the various catheter components may be formed and joined by conventional materials and methods. Outer tubular member 14 can be formed by conventional techniques, such as by extruding and necking materials found useful in intravascular catheters such a polyethylene, polyvinyl chloride, polyesters, polyamide, polyimides, polyurethanes, and composite materials. In one presently preferred embodiment, outer tubular member 14 is a nylon.

The length of the dilatation catheter 10 is generally about 137 to about 145 centimeters, and typically about 140 centimeters for PTCA. The outer tubular member 14 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14 proximal section has an OD of about 0.017 to about 0.034 inch (0.43–0.87 mm), and an inner diameter (ID) of about 0.012 to about 0.022 inch (0.30–0.56 mm). The inner tubular member 16 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 24 is typically about 0.5 to about 6 cm in length, with an inflated working diameter of about 3 to about 10 mm.

While the present invention has been described herein in terms of certain preferred embodiments, those skilled in the art will recognize that modifications and improvements may be made without departing form the scope of the invention. For example, while discussed primarily in terms of a balloon catheter, the coil supported shaft may be used in a variety of catheters including guiding catheters, drug delivery catheters, and the like. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. An intravascular balloon catheter, comprising:
    a) an elongated shaft having an outer tubular member defining an inflation lumen, and an inner tubular member defining a guidewire lumen, the inner tubular member comprising a polymeric tube with at least a section having an outer coiled support member wound in a first direction and embedded in the polymeric tube, and an inner coiled support member wound in a second direction opposite to the first direction and having coils spaced apart and spaced closer together than coils of the outer coiled support member, and the inner coiled support member has an inner surface with a lubricious coating thereon which is a discontinuous lubricious layer, and the outer coiled support member has a pitch which is not greater than about 40 to about 60 degrees with respect to a longitudinal axis of the tube to provide a desired flexibility, and the difference in pitch between the inner and outer coiled support member coils is about 10 to about 45 degrees to provide a desired tensile strength and stiffness; and b) an inflatable balloon on a distal shaft section having an interior in fluid communication with the inflation lumen.

2. The balloon catheter of claim 1 wherein the inner coiled support member is at least partially embedded in the polymeric tube.

3. The balloon catheter of claim 1 wherein the inner coiled support member is partially embedded in the polymeric tube.

4. The balloon catheter of claim 1 wherein the coils of the inner coiled support member are closed together in contact with one another.

5. The balloon catheter of claim 1 wherein the inner coiled support member has an outer surface in contact with an inner surface of the outer coiled support member.

6. The balloon catheter of claim 1 wherein the coils of the inner coiled support member have a spacing therebetween which is constant along the length of the inner coiled support member.

7. The balloon catheter of claim 1 wherein the coils of the outer coiled support member have a spacing therebetween which is constant along the length of the outer coiled support member.

8. The balloon catheter of claim 1 wherein the coils of he inner coiled support member have a pitch which is constant along the length of the inner coiled support member.

9. The balloon catheter of claim 1 wherein the coils of the outer coiled support member have a pitch which is constant along the length of the outer coiled support member.

10. The balloon catheter of claim 1 wherein the pitch of the coils of the outer coiled support member is about 25 to about 45 degrees greater than the pitch of the inner coiled support member.

11. The balloon catheter of claim 1 wherein the pitch of the coils of the inner coiled support member is about 2 to about 15 degrees.

12. The balloon catheter of claim 10 wherein the pitch of the coils of the outer coiled support member is about 25 to about 40 degrees.

13. The balloon catheter of claim 1 wherein the outer and inner coiled support members extend along a length of the inner tubular member which is about 15% to about 100% of the length of the inner tubular member.

14. The balloon catheter of claim 1 wherein the outer and inner coiled support members are formed of wire or ribbon.

15. The balloon catheter of claim 14 wherein the wire or ribbon has a width of about 0.001 to about 0.005 mm.

16. The balloon catheter of claim 1 wherein the inner coiled support member is metal, and the outer coiled support member is a polymeric material.

17. The balloon catheter of claim 1 wherein the inner and outer coiled support members are unifilar.

18. The balloon catheter of claim 17 wherein the coiled support members have a spring rate of about 0.05 to about 1.5 lbs/inch.

19. The balloon catheter of claim 1 wherein the inner coiled support member is unifilar, and the outer coiled support member is multifilar.

20. The balloon catheter of claim 19 wherein the coiled support member has a spring rate of about 0.05 to about 10 lbs/inch.

21. The balloon catheter of claim 1 wherein at least one of the inner and the outer coiled support members is formed of metal.

22. The balloon catheter of claim 1 wherein both the inner and the outer coiled support members are formed of metal.

23. The balloon catheter of claim 1 wherein the outer coiled support member exerts a radially inward force on the inner coiled support member and interlocks therewith when the catheter is under tension.

24. An intravascular balloon catheter, comprising:

a) an elongated shaft having an outer tubular member defining an inflation lumen, and an inner tubular member defining a guidewire lumen, the inner tubular member comprising a polymeric tube with at least a section having an outer coiled support member wound in a first direction and completely embedded in the polymeric tube, and an inner coiled support member wound in a second direction opposite to the first direction and partially embedded in the polymeric tube and having coils which are spaced apart and which are spaced closer together than coils of the outer coiled support member, and a lubricious coating on an inner surface of the inner coiled support member forming a discontinuous lubricious layer; and b) an inflatable balloon on a distal shaft section having an interior in fluid communication with the inflation lumen.

* * * * *

UNITED STATES PATENT AND TRADEMARK OFFICE
CERTIFICATE OF CORRECTION

| | | |
|---|---|---|
| PATENT NO. | : 7,041,125 B2 | Page 1 of 1 |
| APPLICATION NO. | : 10/186769 | |
| DATED | : May 9, 2006 | |
| INVENTOR(S) | : Jason J. Hwang et al. | |

It is certified that error appears in the above-identified patent and that said Letters Patent is hereby corrected as shown below:

Column 9,
Line 28, delete "he" and insert --the--.

Signed and Sealed this

Seventeenth Day of October, 2006

JON W. DUDAS
*Director of the United States Patent and Trademark Office*